United States Patent
Mine (10) Patent No.: US 8,538,100 B2
(45) Date of Patent: Sep. 17, 2013

(54) ULTRASONIC DIAGNOSTIC APPARATUS AND ULTRASONIC IMAGE DISPLAY METHOD

(75) Inventor: Yoshitaka Mine, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1052 days.

(21) Appl. No.: 12/021,734

(22) Filed: Jan. 29, 2008

(65) Prior Publication Data

US 2008/0193004 A1    Aug. 14, 2008

(30) Foreign Application Priority Data

Jan. 30, 2007  (JP) ................. 2007-020056

(51) Int. Cl.
*G06K 9/46* (2006.01)
*G06K 9/68* (2006.01)

(52) U.S. Cl.
USPC ........... 382/128; 382/130; 382/131; 382/155; 382/181; 382/254

(58) Field of Classification Search
USPC ................. 382/128, 130, 131, 155, 181, 254
See application file for complete search history.

(56) References Cited

U.S. PATENT DOCUMENTS

| | | | |
|---|---|---|---|
| 6,335,979 B1 | 1/2002 | Seto et al. | |
| 6,402,693 B1 | 6/2002 | Emery | |
| 2004/0066398 A1 | 4/2004 | Dolimier et al. | |
| 2004/0081340 A1* | 4/2004 | Hashimoto | 382/128 |
| 2004/0116812 A1 | 6/2004 | Selzer et al. | |
| 2007/0127795 A1* | 6/2007 | Lau et al. | 382/128 |
| 2009/0275830 A1* | 11/2009 | Falco et al. | 600/437 |

FOREIGN PATENT DOCUMENTS

| | | |
|---|---|---|
| EP | 0 844 581 A2 | 5/1998 |
| JP | 8-107895 | 4/1996 |
| JP | 9-81646 | 3/1997 |
| JP | 10-179586 | 7/1998 |
| JP | 11-235334 | 8/1999 |
| JP | 2000-132628 | 5/2000 |
| JP | 2002-177214 | 6/2002 |
| JP | 2003-38447 | 2/2003 |
| JP | 2003-216496 | 7/2003 |
| JP | 2004-57356 | 2/2004 |
| JP | 2004-105638 | 4/2004 |
| JP | 2005-85200 | 3/2005 |
| JP | 2006-197968 | 8/2006 |
| JP | 2006-223739 | 8/2006 |
| JP | 2006-285740 | 10/2006 |
| JP | 2007-20755 | 2/2007 |

OTHER PUBLICATIONS

Japanese Office Action mailed Feb. 14, 2012, in Japanese Patent Application No. 2007-020056 filed Jan. 30, 2007 (with English Translation).

* cited by examiner

*Primary Examiner* — Nicole Ippolito

(74) *Attorney, Agent, or Firm* — Oblon, Spivak, McClelland, Maier & Neustadt, L.L.P.

(57) ABSTRACT

In the image acquisition mode, desired past images are registered in an image table. A past image selected from the past images registered in the table is displayed as a reference image together with a live image in a predetermined form. Selecting another image registered in the image table at an arbitrary timing will display another past image upon replacing the reference image.

21 Claims, 11 Drawing Sheets

ULTRASONIC DIAGNOSTIC APPARATUS AND ULTRASONIC IMAGE DISPLAY METHOD

CROSS-REFERENCE TO RELATED APPLICATIONS

This application is based upon and claims the benefit of priority from prior Japanese Patent Application No. 2007-020056, filed Jan. 30, 2007, the entire contents of which are incorporated herein by reference.

BACKGROUND OF THE INVENTION

1. Field of the Invention

The present invention relates to an ultrasonic diagnostic apparatus and ultrasonic image display method which allow easy and simple reference to arbitrary images (past images) acquired or generated in the past, which are typified by ultrasonic images or other modality images (e.g., CT images and MR images), at the time of ultrasonic image diagnosis, medical treatment under the guidance of ultrasonic images, and the like.

2. Description of the Related Art

An ultrasonic diagnostic apparatus is a medical image device which noninvasively obtains a tomogram of soft tissue in a living body from the body surface by an ultrasonic pulse reflection method. This ultrasonic diagnostic apparatus is, for example, smaller in size, more inexpensive, and safer because of no exposure to X-rays than other medical image devices, can perform blood flow imaging, and hence is widely used in a cardiac department, abdominal department, urological department, obsterics and gynecology, and the like.

This ultrasonic diagnostic apparatus has a dual display function as an image display function which simultaneously displays a frozen image and a live image. With this dual display function, when, for example, performing a contrast medium examination immediately before paracentesis, a doctor can puncture a target tumor while seeing a perfusion image of the tumor displayed on one window and a live image on the other window. In addition, for example, while performing medical treatment with a tumor image (past image) before cauterization being displayed on one window, the doctor can determine a treatment effect while comparing with a live image displayed on the other window.

The ultrasonic diagnostic apparatus has a patient browser function as another image display function which is used to browse information (including image information) about a predetermined patient. Using this patient browser function makes it possible to access and check desired B-mode images and contrast-enhanced images in the past when, for example, puncturing a hepatic tumor.

In actual clinical settings, for example, there is a demand to puncture a tumor and determine an effect after medical treatment while comparing a live image with an arbitrary past image typified by a B-mode image, a contrast-enhanced image, or a CT image on a view box, as needed, or to use past images acquired in a plurality of examinations while easily switching the display of images. The conventional ultrasonic diagnostic apparatuses only have the dual display function and the patient browser function in image display but cannot meet the above demand.

BRIEF SUMMARY OF THE INVENTION

The present invention has been made in consideration of the above situation, and has as its object to provide an ultrasonic diagnostic apparatus and ultrasonic image display method which allow to compare and observe a desired image acquired in the past with a live image or a stored image after acquisition, as needed, during tumor paracentesis or the like.

According to an aspect of the present invention, it is provided that an ultrasonic diagnostic apparatus which comprises: a selection unit which is configured to select at least one of past images acquired in the past from an image storage management unit in the ultrasonic diagnostic apparatus, an image recording medium connected to the apparatus, and an image storage management system connected via a network; a reference image registration unit which is configured to register a selected image in an image list for image reference together with information about a storage location of the image; an acquisition unit which acquires the image registered in the image list on the basis of the information about the storage location and stores the image in an image storage management unit in the ultrasonic diagnostic apparatus; and a display unit which arbitrarily repeatedly displays the acquired past image in the reference list as a reference image.

According to another aspect of the present invention, it is provided that an ultrasonic image display method which comprises: registering at least one past image acquired in the past in an image table and storing information about a storage location of the registered past image; selecting a desired past image from the registered past images; acquiring the selected past image from the storage location on the basis of the information about the storage location; and displaying the acquired past image as a reference image together with a live image.

DETAILED DESCRIPTION OF THE INVENTION

An embodiment of the present invention will be described below with reference to the views of the accompanying drawing. Note that in the following description, the same reference numerals denote constituent elements having almost the same functions and arrangements, and a repetitive description will be made only when required.

Figure 1:
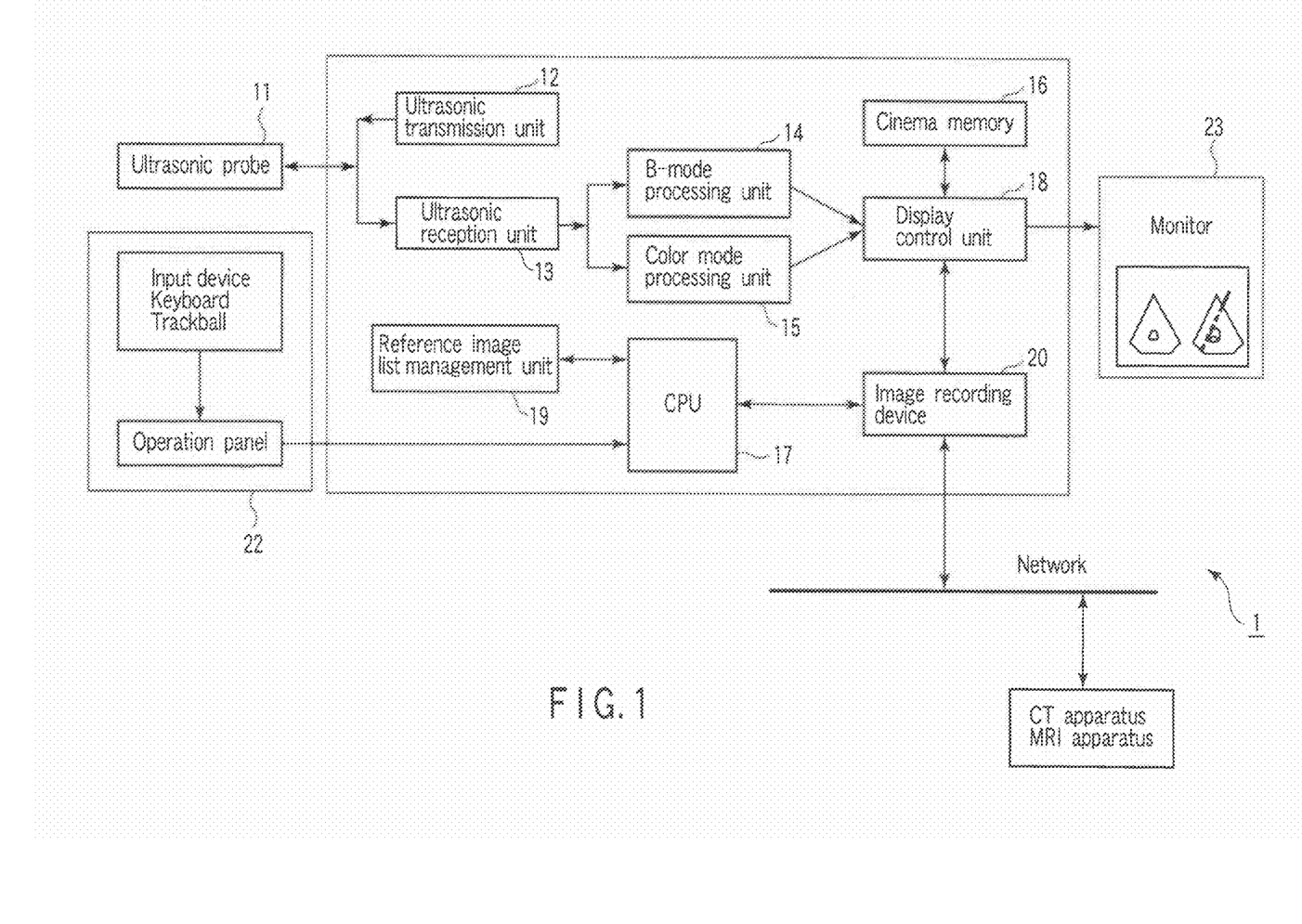
FIG. 1 is a block diagram showing the arrangement of an ultrasonic diagnostic apparatus 1 according to this embodiment.

FIG. 1 is a block diagram showing the arrangement of an ultrasonic diagnostic apparatus 1 according to this embodiment. As shown in FIG. 1, the ultrasonic diagnostic apparatus 1 comprises an ultrasonic probe 11, ultrasonic transmission unit 12, ultrasonic reception unit 13, B-mode processing unit 14, color mode processing unit 15, cinema memory 16, control unit (CPU) 17, display control unit 18, reference image list management unit 19, image recording device 20, operation unit 22, and monitor 23.

The ultrasonic probe 11 includes a plurality of piezoelectric transducers which generate ultrasonic waves on the basis of driving signals from the transmission unit 12 and convert reflected waves from a subject to be examined into electrical signals, a matching layer provided for the piezoelectric transducers, a backing member which prevents ultrasonic waves from propagating backward from the piezoelectric transducers, and the like. When ultrasonic waves are transmitted from the ultrasonic probe 11 to the subject, various harmonic components are generated due to the nonlinearity of a living tissue along the propagation of the ultrasonic waves. Fundamental waves and harmonic components constituting transmission ultrasonic waves are scattered backward by acoustic impedance boundaries of a tissue in a living body, micro-scattering, and the like, and are received as reflected waves (echoes) by the ultrasonic probe 11.

The ultrasonic transmission unit 12 includes a delay circuit, a pulser circuit, and the like (not shown). The pulser circuit repetitively generates rate pulses for the formation of transmission ultrasonic waves at a predetermined rate frequency fr Hz (period: 1/fr sec). The delay circuit gives each rate pulse a delay time necessary to focus an ultrasonic wave into a beam and determine transmission directivity for each channel. The transmission unit 12 applies a driving pulse to each vibrator so as to form an ultrasonic beam toward a predetermined scan line at the timing based on this rate pulse.

The ultrasonic reception unit 13 includes an amplifier circuit, A/D converter, adder, and the like (not shown). The amplifier circuit amplifies an echo signal received via the probe 11 for each channel. The A/D converter gives the amplified echo signals delay times necessary to determine reception directivities. The adder then performs addition processing for the signals. With this addition, an ultrasonic echo signal corresponding to a predetermined scan line is generated.

Note that the a T/R switch (not shown) is used to switch connection between the ultrasonic probe 11, ultrasonic transmission unit 12, and ultrasonic reception unit 13 at the time of transmission and reception.

The B-mode processing unit 14 performs envelope detection processing for the ultrasonic echo signal received from the reception unit 13 to generate a B-mode signal or the like corresponding to the amplitude intensity of the ultrasonic echo.

The color mode processing unit 15 performs quadrature detection processing, autocorrelation processing, and the like for the echo signal received from the reception unit 13, and obtains a tissue Doppler signal corresponding to the velocity, variance, and power of the tissue which moves in the subject on the basis of the Doppler shift component of the ultrasonic echo signal having undergone delay/addition processing.

The cinema memory 16 is, for example, a memory which stores ultrasonic images corresponding to a plurality of frames immediately before freezing. Continuous display (cinema display) of the images stored in the cinema memory 16 makes it possible to display an ultrasonic moving image.

The control unit 17 functions as an information processing apparatus (computer) and statically or dynamically controls the operation of this ultrasonic diagnostic apparatus.

The display control unit 18 generates a B-mode ultrasonic image, Doppler image, or the like which represents a dimensional distribution associated with a predetermined slice of a B mode signal. The display control unit 18 performs image processing for a reference image to match its observation angle, magnification, positional relationship, and the like with those of a live image in an image comparison mode (to be described later).

The reference image list management unit 19 executes processing associated with an image acquisition mode and image reference mode (to be described later) by unarchiving predetermined programs in a memory under the control of the control unit 17.

The image recording device 20 stores ultrasonic images acquired by the ultrasonic diagnostic apparatus, an image table generated in the image acquisition mode (to be described later), information (storage location information) about the storage locations of past images registered in the image table, and the like. Note that the ultrasonic image data which the operation unit 22 stores can be so-called raw image data before scan conversion.

The operation unit 22 is connected to the apparatus body and includes a mouse, trackball, mode switch, keyboard, and the like which are used to input, to the apparatus body, various instructions from the operator, an instruction to set a region of interest (ROI), various image quality setting instructions, and the like.

The monitor 23 displays morphological information and blood flow information in the living body as images on the basis of video signals from the display control unit 18. The monitor 23 displays an image table, a past image registered in the image table, information about the past image, a reference image, a live image, and the like in predetermined forms in the image acquisition mode and image comparison mode (to be described later) under the control of the control unit 17.

(Image Acquisition Mode and Image Reference Mode)

Operation in the image acquisition mode and image comparison mode which the ultrasonic diagnostic apparatus 1 has will be described next. In this case, the image acquisition mode (Acquisition Mode) is an operation form of registering desired past images, in the image table, which are displayed together with live images during imaging so as to be used as references for paracentesis and treatment effect determination. The image comparison mode (Comparison Mode) is an operation form of displaying an image (reference image) selected from the past images registered in the image table together with a live image in a predetermined form. Each mode will be described in detail below by taking, as an example, a case in which each mode is used for paracentesis.

(Image Acquisition Mode)

Figure 2:
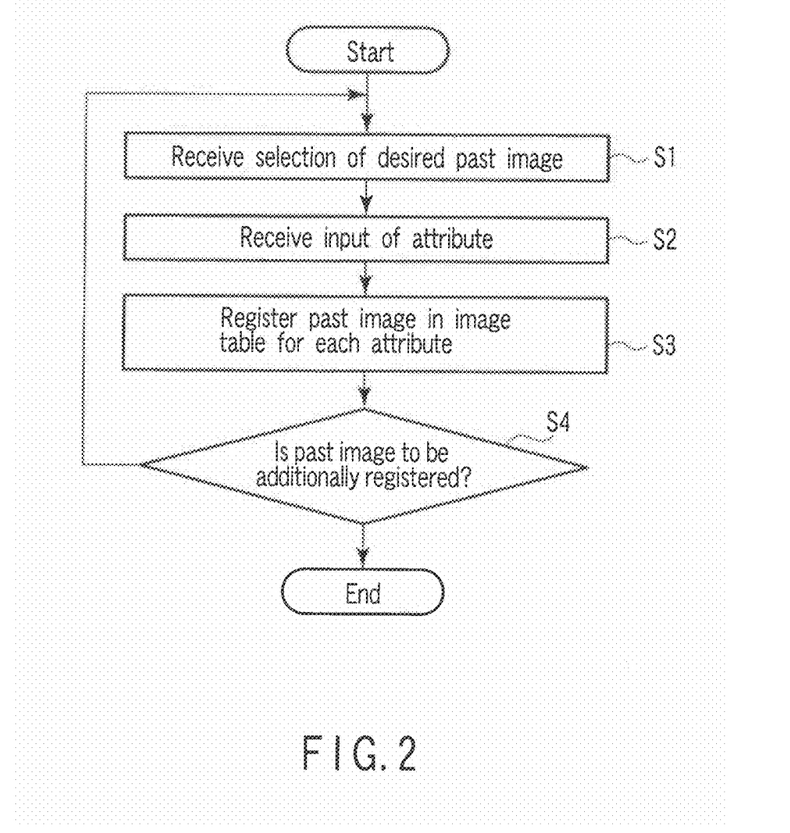
FIG. 2 is a flowchart showing an example of a processing procedure executed in an image acquisition mode.

FIG. 2 is a flowchart showing an example of a processing procedure executed in the image acquisition mode. As shown in FIG. 2, first of all, a past image which is likely to serve as a reference in paracentesis is selected from the past images stored in an image server on a network, an image storage device in another modality, the image recording device 20 which the ultrasonic diagnostic apparatus 1 has, or the like (step S1).

Figure 3:
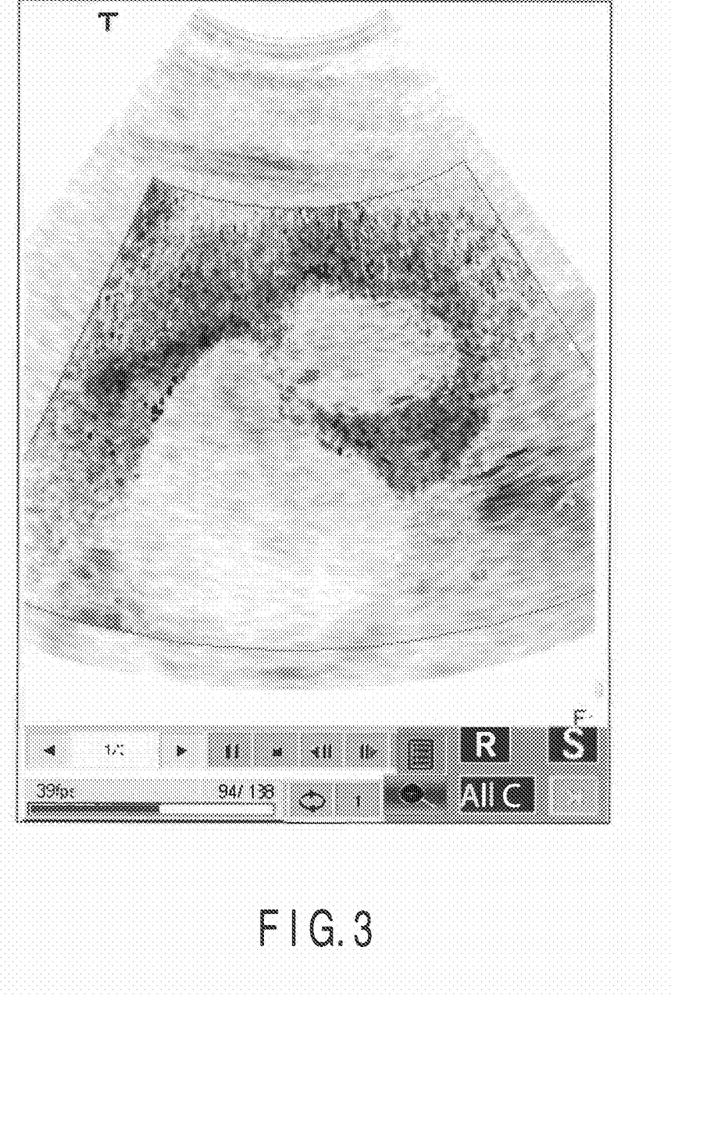
FIG. 3 is a view showing an example of a past image registered in an image table.
Figure 4:
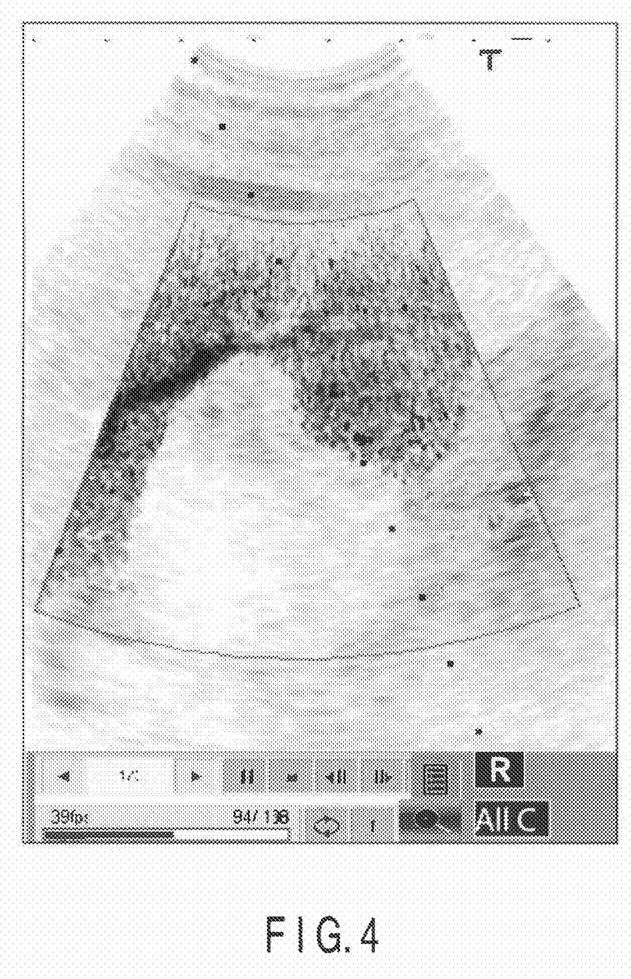
FIG. 4 is a view showing another example of the past image registered in the image table.

Note that in this selection of a past image, it is possible to set, as selection targets, not only past images associated with the same patient but also past images of another person obtained by applying medical treatment to the same disease in the same region by using pieces of DICOM header information and the like. Therefore, for example, as shown in FIGS. 3 and 4, it is possible to select past images of another person before and after paracentesis treatment for a predetermined morbid portion.

In addition, selectable past images are not limited to ultrasonic images. That is, it is possible to select past images acquired by other modalities (e.g., CT images and MR images). Sample images, animation images, and the like can also be used. Furthermore, past images can be two-dimensional images, two-dimensional moving images, three-dimensional images, or three-dimensional moving images.

The operator then inputs an attribute associated with the selected past image (step S2). The selected past image is classified according to the attribute and registered, and the storage location information of the past image is stored (step S3). In this case, an attribute is a label which the operator can arbitrarily input to classify and manage the past image registered in the image table. Note that it is not essential to input an attribute, and it is possible to omit this operation if there is no need for classification.

When another past image is to be additionally registered in the image table, the processing in steps S1 to S3 is repeatedly executed. If there is no past image to be added, the image acquisition mode is terminated (step S4).

Note that the operator can clear the image table with predetermined operation at an arbitrary timing. When the process shifts to a new examination (medical treatment), the image table is automatically reset. When a past image is newly registered in the reset or cleared image table afterward, the processing in steps S1 to S4 is repeatedly executed.

(Image Comparison Mode)

Figure 5A:
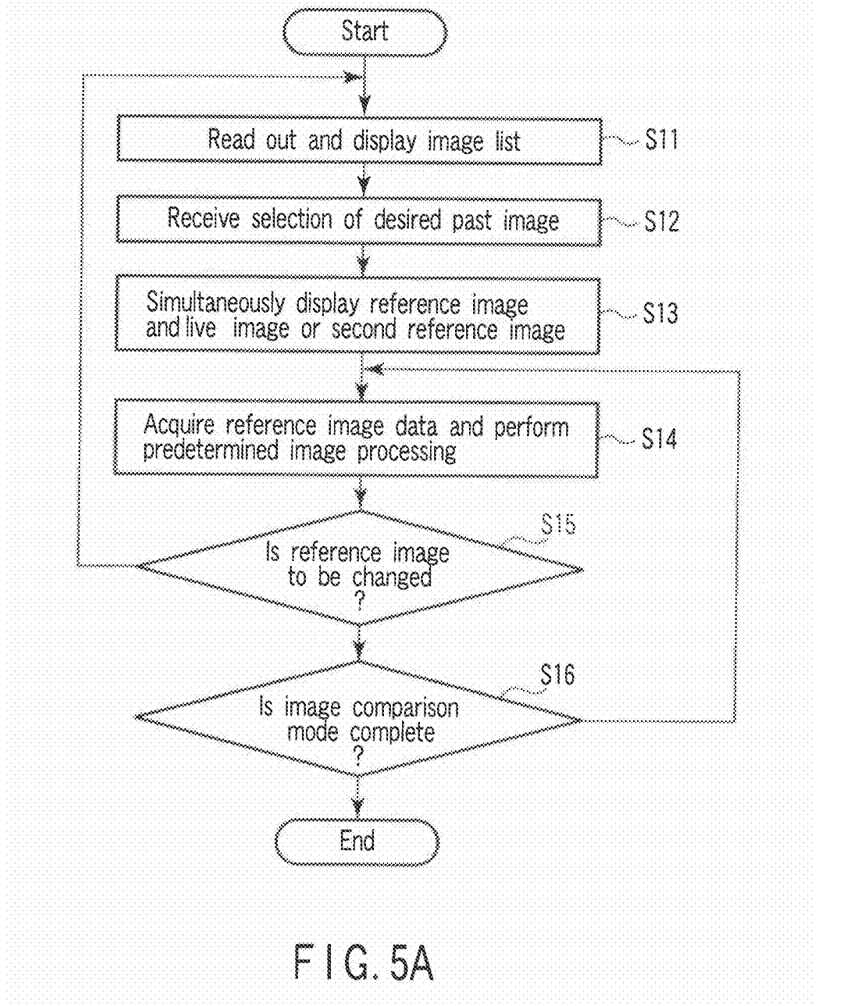
FIG. 5A is a flowchart showing an example of a processing procedure executed in an image comparison mode.
Figure 5B:
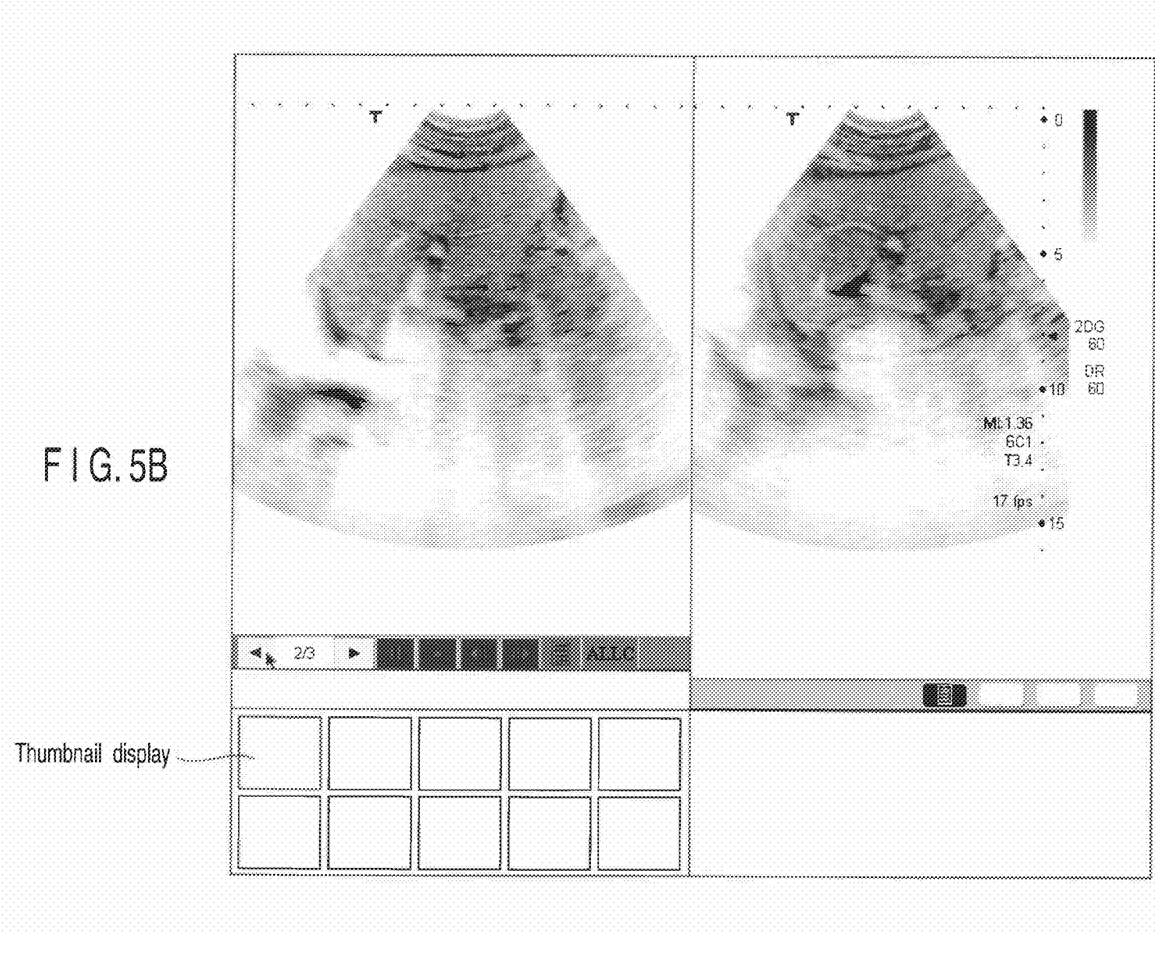
FIG. 5B is a view showing an example of a display form in the image comparison mode.
Figure 5C:
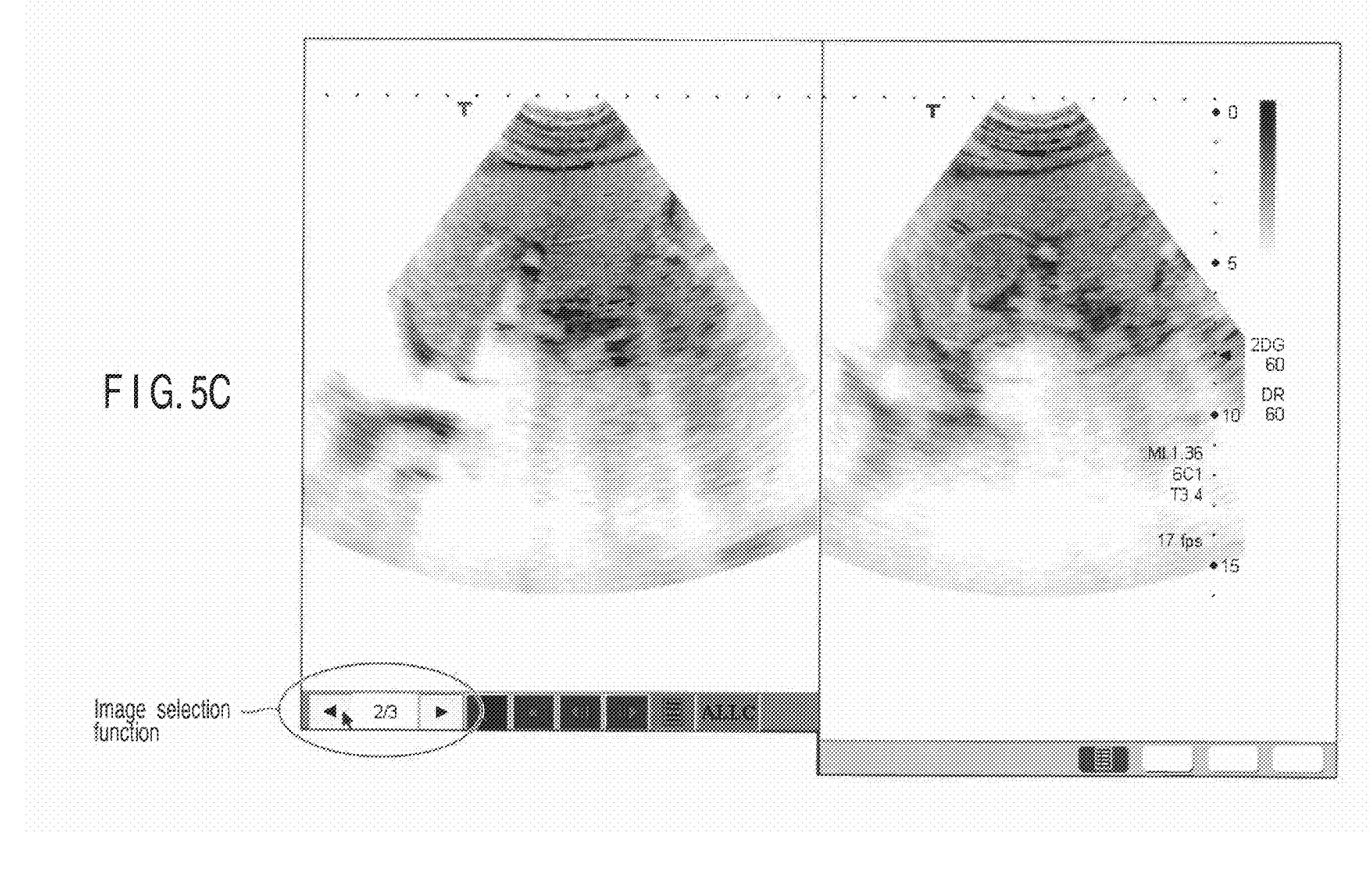
FIG. 5C is a view showing another example of the display form in the image comparison mode.

FIG. 5A is a flowchart showing an example of a processing procedure executed in the image comparison mode. As shown in FIG. 5A, first of all, the image table generated in the image acquisition mode is read out, and registered past images are displayed (step S11). The registered past images can be displayed in any form as long as the operator can grasp the contents of the images. Typical examples of such form include thumbnail display (see FIG. 5B), individual display (see FIG. 5C) in which images are displayed while being manually or automatically switched one by one, list display using text information indicating the storage location information of each image or attributes of each image (e.g., patient information, an examination name, an examination region, an imaging modality, an examination date, examiner, and the like), and the like.

Upon receiving selection of a desired past image via the operation unit 22 (step S12), the control unit 17 acquires the image from a predetermined location on the basis of the storage location information of the selected past image.

Figure 6:
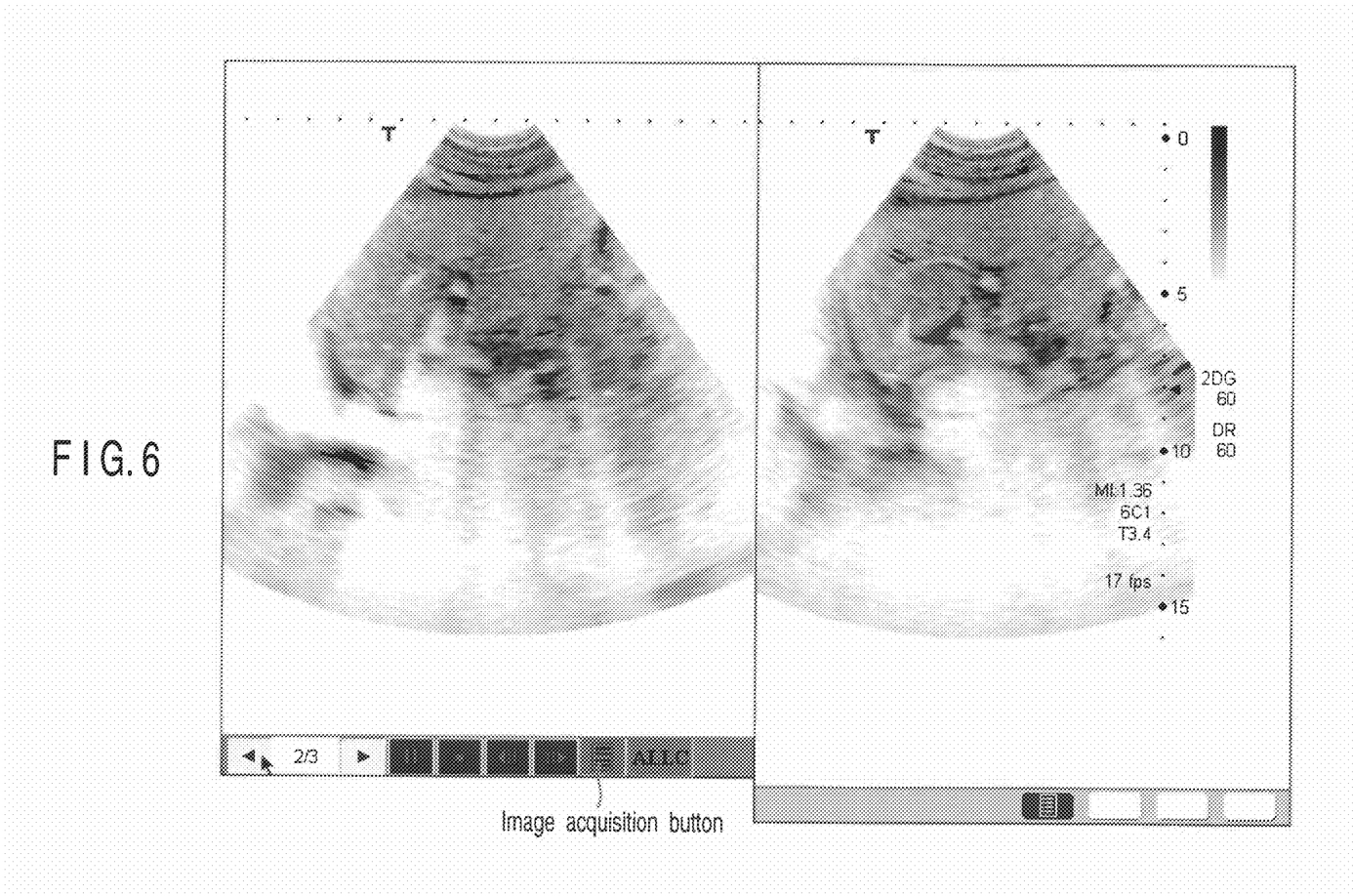
FIG. 6 is a view showing a display example in the image comparison mode when a reference image is a past ultrasonic image.
Figure 7A:
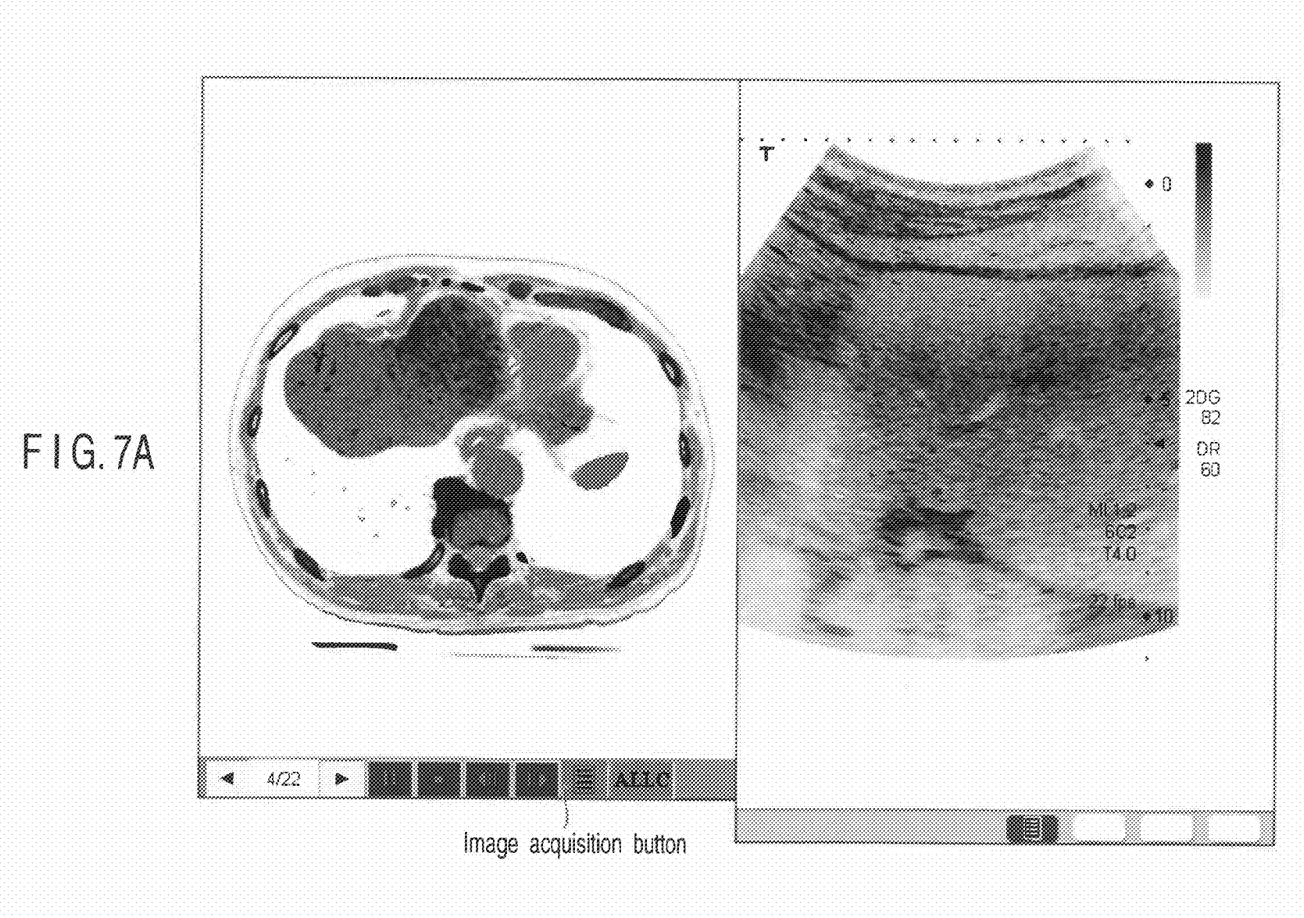
FIG. 7A is a view showing a display example in the image comparison mode when a reference image is a past CT image.
Figure 7B:
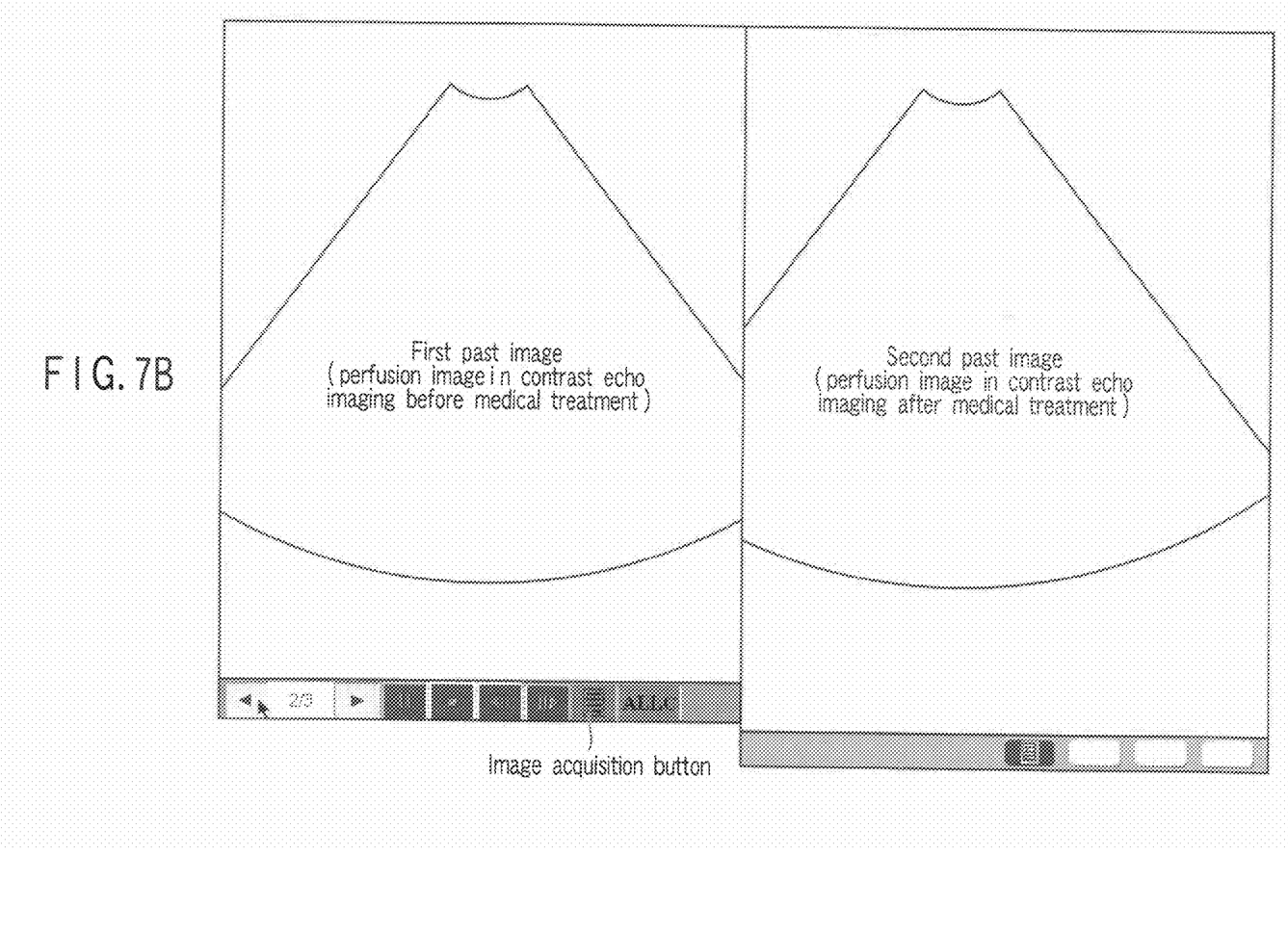
FIG. 7B is a view showing an example of displaying two past images generated in the same procedure side by side.

A reference image having undergone predetermined image processing is displayed on the monitor 23 together with a live image (step S13). FIG. 6 shows a display example in the image comparison mode in a case in which a reference image is a past ultrasonic image. FIG. 7A shows a display example in the image comparison mode in a case in which a reference image is a past CT image. The doctor can perform paracentesis while observing the reference image and the live image which are displayed in the form shown in each of the drawings. FIG. 7B shows an example of displaying the first and second past images generated in the same procedure as that described above side by side. As the second past image, for example, a reference image is registered independently of the first past image. In the example in FIG. 7B, perfusion images in contrast echo imaging before and after medical treatment are respectively displayed as the first and second past images so as to be compared with each other.

The display control unit 18 then performs predetermined image processing for the acquired past image (step S13). In this case, the predetermined image processing includes the processing of matching an observation angle, magnification, positional relationship, temporal information, and the like between the reference image and the live image and the processing of matching a luminance, dynamic range, and image filter between the reference image and the live image. For example, the display control unit 18 executes positional relationship matching with reference to a plurality of characteristic regions designated in advance. If a reference image is a moving image, for example, the display control unit 18 executes this processing with reference to an image subjectively determined as an equivalent frame by the operator. If, for example, a treatment target is the heart and a reference image is matched with information about a cardiac time phase, temporal information matching is executed to match the cardiac time phase of the reference image with that of the live image or the second reference image.

When the sameness of a patient is required between a reference image and a live image, the control unit 17 checks the sameness before step S13 by comparing a patient ID added as the header information of the reference image with the patient ID of the patient currently diagnosed. The control unit 17 can display the patient ID (or information for specifying the patient) added to a reference image together with the reference image, as needed.

When the displayed reference image is to be changed, the processing from step S11 to step S14 is repeatedly executed (step S15). If the medical treatment using the display reference image is complete and an end instruction is issued, the image comparison mode is terminated (step S16).

(Application)

An application associated with the image acquisition mode and image comparison mode of the ultrasonic diagnostic apparatus 1 will be described next.

Figure 8:
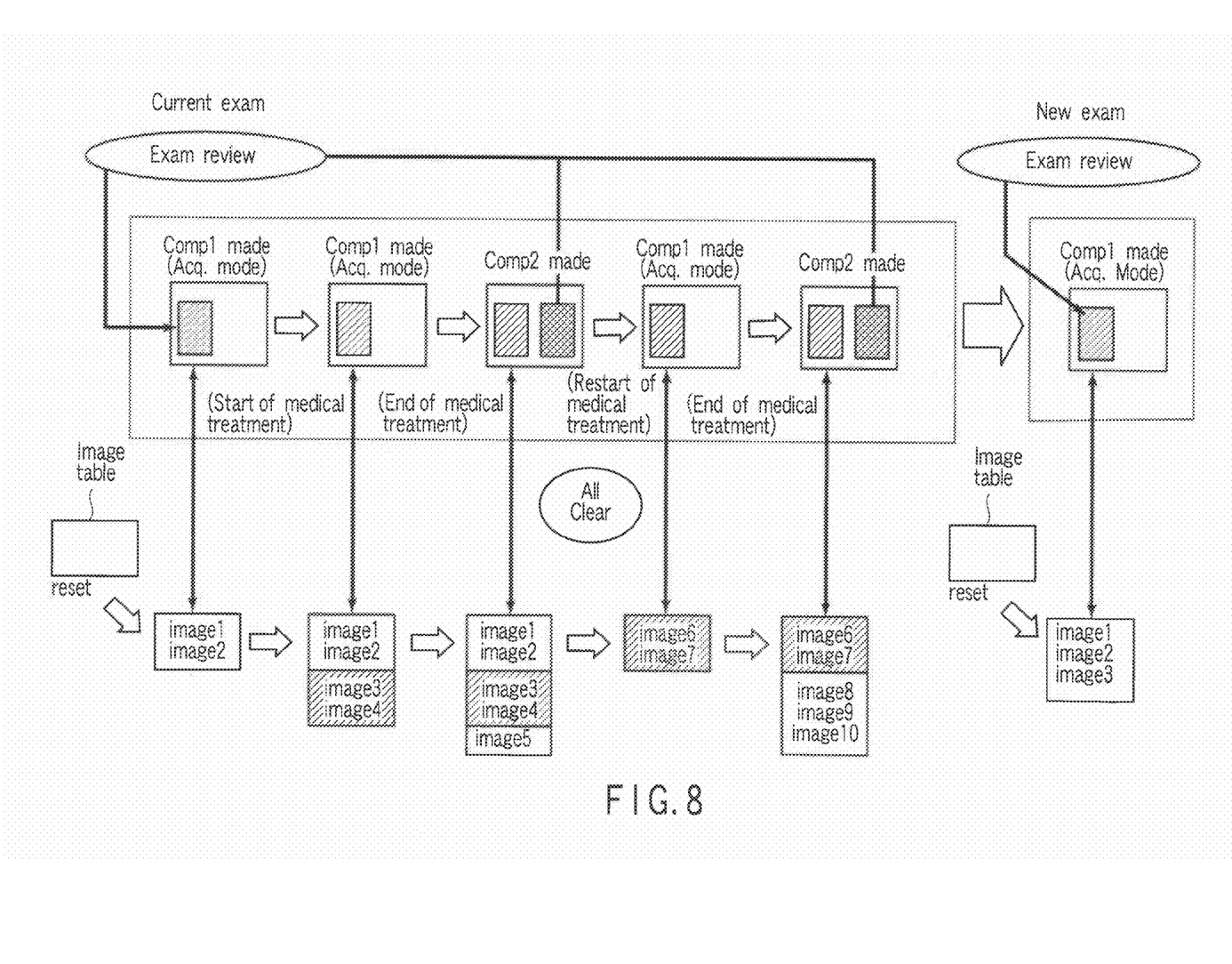
FIG. 8 is a view for explaining an example of an application associated with the image acquisition mode and image comparison mode.

FIG. 8 is a view for explaining an example of an application associated with the image acquisition mode and image comparison mode. As shown in FIG. 8, the image comparison mode of displaying a past image and a live image is activated. As shown in FIG. 6, when the operator presses an image acquisition button during Comp1 Mode, the current mode shifts to the image acquisition mode. The processing from step S1 to step S4 shown in FIG. 2 is then executed to generate an image table in which image 1 and image 2 are registered. During Comp1 Mode, image 1 or image 2 is selected and displayed as a past image on the left window, and a live image is displayed on the right window. In the steps shown in FIG. 5A, the above display is executed, and the image size and position are also adjusted.

After medical treatment, the image comparison mode in which the first and second past images are displayed side by side is activated. The processing in steps S11 to S16 is executed for the first and second past images to display the first reference image together with the second past image for the determination of the treatment effect of paracentesis in a predetermined form.

All the past images registered in the image table in the image comparison mode (Comp1 Mode) are cleared (ALL Clear). In the image acquisition mode, an image table in which image 6 and image 7 are classified as images with the same attribute is generated again. When an examination (medical treatment) is resumed, a reference image is displayed together with a live image for monitoring paracentesis in a predetermined form. This image comparison mode exemplifies a case in which the image acquisition mode is activated during paracentesis, and images (image 8 to image 10) required to indicate the state of paracentesis are newly registered in the image table. In the above case, all the past images are cleared (All Clear). In some cases, unnecessary images are partly deleted (edited).

When an examination (medical treatment) is to be performed on a new patient, the image table is automatically reset, and the same processing is repeatedly executed.

According to the above arrangement, the following effects can be obtained.

According to this ultrasonic diagnostic apparatus, in the image acquisition mode, a desired past image is registered in the image table. This apparatus displays a past image selected from the past images registered in the table as a reference image together with a live image in a predetermined form. In addition, selecting another image registered in the image table at an arbitrary timing makes it possible to display another past image upon replacing the reference image with it. When, therefore, determining an effect after medical treatment in puncturing a tumor, an operator such a doctor can compare and observe a live image and a desired past image, as needed. This makes it possible to provide effective medical information in a suitable form and contribute to safe paracentesis, reliable treatment effect determination, and the like.

This ultrasonic diagnostic apparatus also allows to register only desired images in the image table in the image acquisition mode. This saves the doctor from having to see any unnecessary images during image diagnosis without much time to spare. This can therefore reduce the operation load on an operator such as a doctor during image diagnosis.

It is possible to execute the image acquisition mode and image comparison mode of this ultrasonic diagnostic apparatus at arbitrary timings. Even if it suddenly becomes necessary to execute such a mode during image diagnosis, it is possible to quickly and easily display a past image and a live image in a form that allows comparison. In addition, this ultrasonic diagnostic apparatus allows the image table to be reset at an arbitrary timing. Even if, therefore, a registered reference image is not suitable for comparison with a live image, suitable image diagnosis can be executed by activating the image acquisition mode after resetting or clearing the image table, and then quickly generating a new image table.

In addition, this ultrasonic diagnostic apparatus displays a reference image and a live image in a form that matches a positional relationship, observation angle, temporal information, magnification, and the like between them. Even if, therefore, magnifications, observation angles, modalities by which a live image and a reference image have been acquired, and the like differ between the live image and the reference image, it is possible to compare and observe them in a suitable form, thereby providing effective medical information.

The present invention is not limited to the above embodiment, and constituent elements can be modified and embodied in the execution stage within the spirit and scope of the invention. The following are concrete modifications.

(1) Each function associated with this embodiment can also be implemented by installing programs which execute equivalent processing in a computer such as a workstation and unarchiving them in a memory. In this case, the programs which can cause the computer to execute the corresponding techniques can be distributed by being stored in recording media such as magnetic disks (floppy (registered trademark) disks, hard disks, and the like), optical disks (CD-ROMs, DVDs, and the like), and semiconductor memories.

(2) The above embodiment is configured to store link information indicating the storage location of each image together with an image table. However, the present invention is not limited to this, and an image table can be generated and managed with image data themselves being attached thereto.

(3) The respective functions described in the above embodiment can also be used in combination with the functions of an existing ultrasonic diagnostic apparatus. For example, if past images registered in the image table have been acquired by different modalities, it is possible to perform predetermined conversion processing for each past image on the basis of DICOM header information attached thereto, store the resultant image in the image recording device 20, and browse them by using the patient browser function.

In addition, various inventions can be formed by proper combinations of a plurality of constituent elements disclosed in the above embodiments. For example, several constituent elements may be omitted from all the constituent elements disclosed in the above embodiments. Furthermore, constituent elements in the different embodiments may be properly combined.

What is claimed is:

1. An ultrasonic diagnostic apparatus comprising:
    a selection unit which is configured to select at least one of past images acquired in the past from an image storage management unit in the ultrasonic diagnostic apparatus, an image recording medium connected to the apparatus, and an image storage management system connected via a network;
    a reference image registration unit which is configured to register a selected image in an image list for image reference together with information about a storage location of the image;
    an acquisition unit which acquires the image registered in the image list on the basis of the information about the storage location and stores the image in an image storage management unit in the ultrasonic diagnostic apparatus; and
    a display unit which arbitrarily repeatedly displays the acquired past image in the reference list as a reference image side by side with a live image,
    wherein the display unit executes image processing to the reference image based on image processing to the live image, and
    wherein the display unit executes the image processing in which at least one of a luminance and dynamic range of the reference image is adjusted so as to correspond to the live image.

2. An apparatus according to claim 1, wherein the display unit displays the reference image together with an ultrasonic live image or a frozen image.

3. An apparatus according to claim 1, which further comprises an input unit which inputs an attribute for said each registered past image, and in which
    the registration unit registers the past image in the image list upon classifying the image according to the input attribute.

4. An apparatus according to claim 1, wherein the registration unit edits or resets the image list at an arbitrary timing in response to manual operation of an operator.

5. An apparatus according to claim 1, wherein the registration unit edits or resets the image list for each examination.

6. An apparatus according to claim 1, which further comprises a determination unit which determines, on the basis of patient information attached to the acquired past image, whether the acquired past image is acquired from the patient, and in which the display unit displays a determination result obtained by the determination unit.

7. An apparatus according to claim 1, wherein the display unit generates and displays the reference image by performing predetermined image processing for the acquired past image.

8. An apparatus according to claim 1, wherein the display unit displays the reference image and the live image in synchronism with each other so as to match temporal information or spatial information therebetween.

9. An apparatus according to claim 1, wherein the display unit displays, based on selection by the selection unit, at least one of a thumbnail image of a past image registered in the image table, information about the storage location of the past image registered in the image table, and information representing an attribute of the past image registered in the image table.

10. An apparatus according to claim 1, wherein
when another past image is selected from the registered past images by the selection unit at an arbitrary timing, the acquisition unit acquires the selected other past image from the storage location on the basis of the information about the storage location, and
the display unit displays the acquired other past image as the reference image.

11. An ultrasonic image display method comprising:
registering at least one past image acquired in the past in an image table and storing information about a storage location of the registered past image;
selecting a desired past image from the registered past images;
acquiring the selected past image from the storage location on the basis of the information about the storage location; and
displaying the acquired past image as a reference image together with a live image side by side,
wherein in the display, executing image processing to the reference image based on image processing to the live image, and
wherein the display unit executes the image processing in which at least one of a luminance and dynamic range of the reference image is adjusted so as to correspond to the live image.

12. A method according to claim 11, which further comprises inputting an attribute for said each registered past image, and in which
in the registration, the past image is registered in the image table upon being classified according to the input attribute.

13. A method according to claim 11, wherein the registration, the image table is edited or reset at an arbitrary timing in response to manual operation of an operator.

14. A method according to claim 11, wherein in the registration, the image table is edited or reset for each examination.

15. A method according to claim 11, which further comprises determining, on the basis of patient information attached to the acquired past image, whether the acquired past image is acquired from the patient, and in which
in the display, a determination result obtained in the determination is displayed.

16. A method according to claim 11, wherein in the display, the reference image is generated and displayed by performing predetermined image processing for the acquired past image.

17. A method according to claim 11, wherein in the display, the reference image and the live image are displayed in synchronism with each other so as to match temporal information or spatial information therebetween.

18. A method according to claim 11, wherein the display displays, based on the selecting, at least one of a thumbnail image of a past image registered in the image table, information about the storage location of the past image registered in the image table, and information representing an attribute of the past image registered in the image table.

19. A method according to claim 11, wherein
in the acquisition, when another past image is selected from the registered past images at an arbitrary timing, the selected other past image is acquired from the storage location on the basis of the information about the storage location, and
in the display, the acquired other past image is displayed as the reference image.

20. The ultrasonic diagnostic apparatus according to the claim 1, wherein the display unit executes the image processing in which at least one of an observation angle, magnification, and positional relationship between the reference image and a live image are matched.

21. The ultrasonic diagnostic apparatus according to the claim 1, wherein the display unit executes the image processing of the reference image by using a filter which is used in filter processing of the live image.

* * * * *